Figure 1:
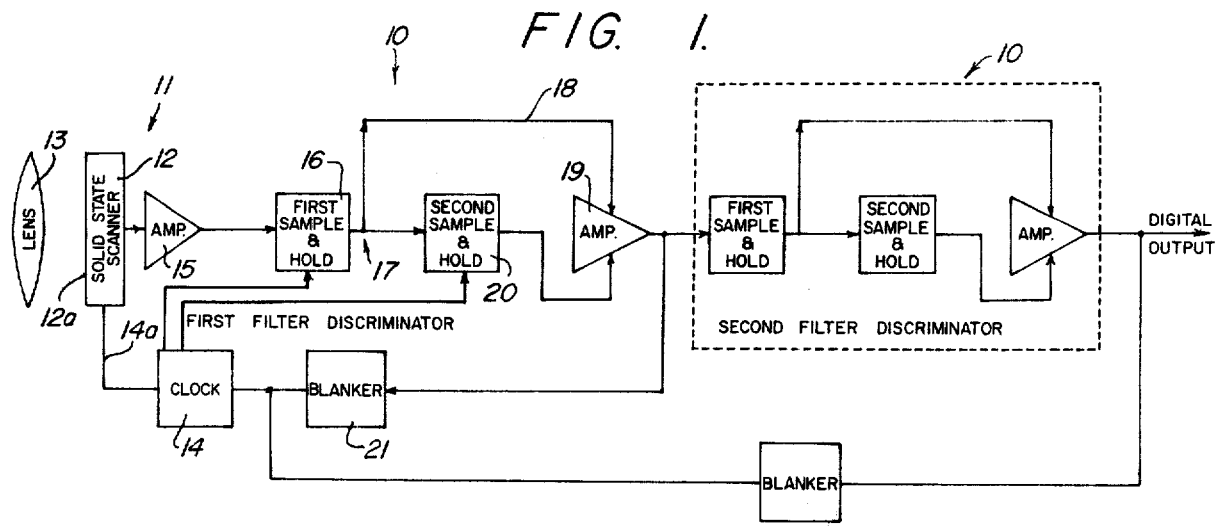

United States Patent [19]

Gomm et al.

[11] 3,932,767

[45] Jan. 13, 1976

[54] FILTER-DISCRIMINATOR CIRCUIT

[75] Inventors: Thiel J. Gomm, Castle Rock; Stephen E. Price, Lakewood, both of Colo.

[73] Assignee: Continental Charter Corporation, Arvada, Colo.

[22] Filed: July 23, 1973

[21] Appl. No.: 381,550

[52] U.S. Cl............. 307/235 R; 328/117; 328/120; 328/151
[51] Int. Cl.² ......................................... H03K 5/20
[58] Field of Search............. 328/58, 110, 115–117, 328/119, 120, 151; 307/235 R

[56] References Cited
UNITED STATES PATENTS

| | | | |
|---|---|---|---|
| 3,116,458 | 12/1963 | Margopoulos | 328/151 X |
| 3,508,158 | 4/1970 | Marchese | 328/151 X |

*Primary Examiner*—John Zazworsky
*Attorney, Agent, or Firm*—K. S. Cornaby

[57] ABSTRACT

A train of pulses introduced into a filter-discriminator circuit is processed therein, the amplitudes of adjacent pulses in the input train being compared against one another deriving an output signal from that comparison whose amplitudes equal the differences in amplitude between adjacent pulses. Adjacent pulses in the train of like amplitude, produce only low amplitude transient signals that are mostly blanked out by circuitry within the discriminator. By connecting a second filter-discriminator circuit in series with the first, the output therefrom will produce a signal having peak or spike pulses therein whose amplitudes equal the double derivative of unlike pulses in the train of pulses. The output peak of spike pulses can then be used as trigger pulses keying timer and associated circuitry.

4 Claims, 3 Drawing Figures

3,932,767

FILTER-DISCRIMINATOR CIRCUIT

BRIEF DESCRIPTION OF THE INVENTION

1. Field of the Invention

This invention relates to circuitry for comparing adjacent pulses in a train of pulses.

2. Prior Art

The present invention provides simple circuitry for discriminating between repetitive signals whose individual amplitudes vary according to certain sensed data or conditions. While circuits such as that shown in U.S. Pat. No. 3,586,864, and some of the other patents disclosed in our co-pending application for U.S. Patent for our Perturbation Detector, are capable of storing data and even comparing that data against model or other data, none of the circuits within our knowledge, prior to the present invention, provides circuitry like that of the present invention. Specifically, unlike the prior art, the present invention involves first and second sample and hold circuits whose products are compared against one another by a difference amplifier that will output a signal containing pulses whose amplitudes are the product of comparing differences in amplitude of adjacent input signal pulses.

SUMMARY OF THE INVENTION

It is a principal object of the present invention to provide circuitry for separating amplitude modulated signals off from a carrier.

Another object is to provide circuitry for comparing adjacent pulses in a train of pulses thereby producing a signal output from that comparison having pulses whose amplitudes reflect differences in amplitude between adjacent input pulses in the train.

Another object is to provide circuitry for shifting in time an input signal such that the pulses in the input signal can be compared against adjacent pulses in that signal, the product of which comparison being signal pulses having amplitudes that equal the differences between adjacent input pulses in the train.

Still another object is to provide a circuit formed from commonly known and commercially available components, which components are connected together into a new and unique circuit.

Still another object is to provide a filter-discriminator circuit that will produce an output signal that is useful for appropriately triggering connected electrical devices, which filter-discriminator circuit can be connected in series to a second such circuit to provide further signal refinement equalizing a double derivative of the input signal.

Principal features of the present invention in a filter-discriminator circuit include, a first sample and hold circuit receiving a signal consisting of a train of pulses. The first sample and hold circuit provides a signal processing whereby the pulses are extended individually into a signal made up of block waves. Circuitry is provided in the present invention for passing the output of the first sample and hold circuit to one side of a difference amplifier and simultaneously to a second sample and hold circuit. Within the second sample and hold circuit the received signal is delayed by approximately the time period of one pulse, and thence travels into the difference amplifier, entering opposite to the input signal from the first sample and hold circuit.

Within the difference amplifier the signals from the first and second sample and hold circuits are compared, adjacent pulses of different amplitudes in the pulse train being examined at specific time intervals to produce a signal output having peaks or spikes whose amplitude equals the amplitude differences sensed in the comparison of adjacent pulses. The output from the difference amplifier is then further processed to eliminate transient signals. A clock is provided to synchronize the input train of pulses with the signal as it is processed within the first and second sample and hold circuits and for synchronizing blanking pulses that are generated to eliminate transient signals from the output of the difference amplifier. The clock of the present invention is the same as or is timed with the clock of the Perturbation Detector of our copending application for patent that provides signals for serially interrogating a scanning array of photo sensitive devices that will produce from such interrogation, a train of pulses for discrimination within the circuit of the present invention.

Further objects and features of the present invention will become apparent from the following detailed description, taken together with the accompanying drawings.

THE DRAWINGS

Figure 3:
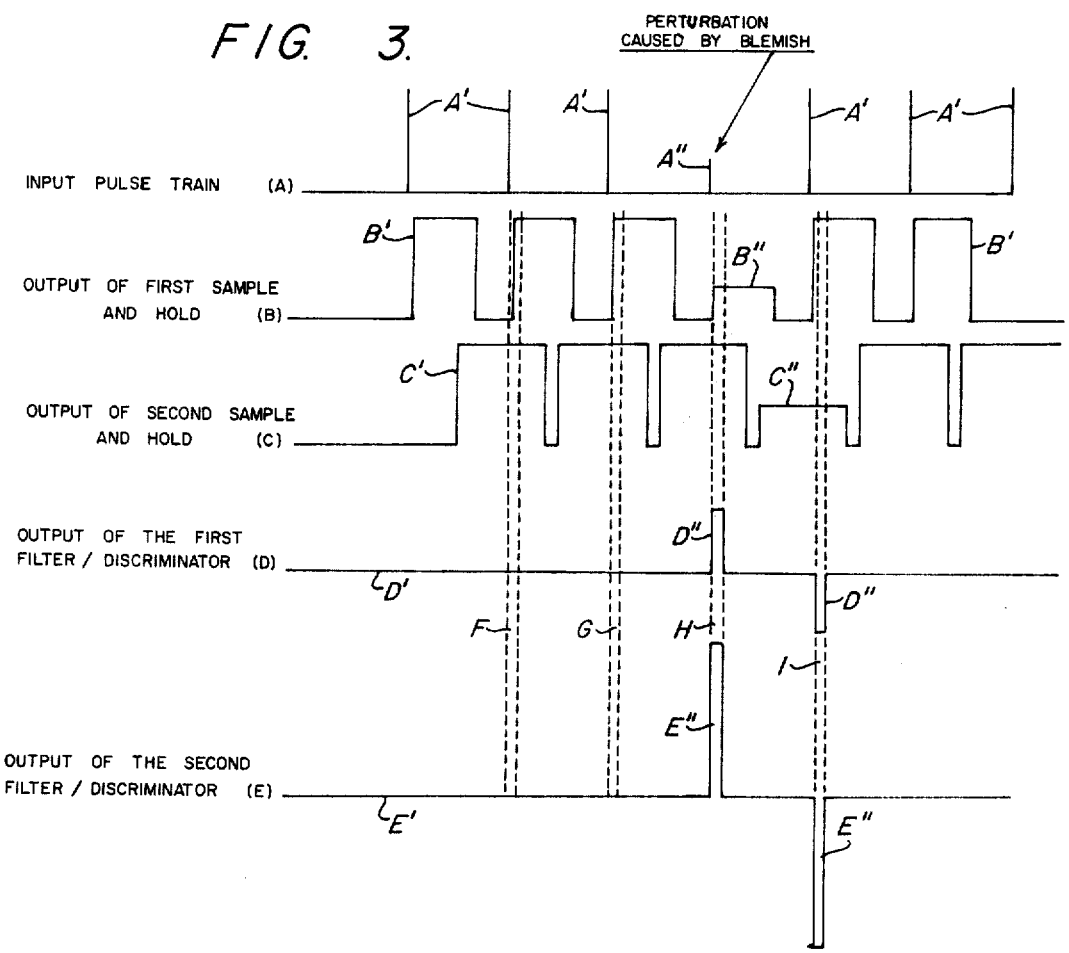
Figure 2:
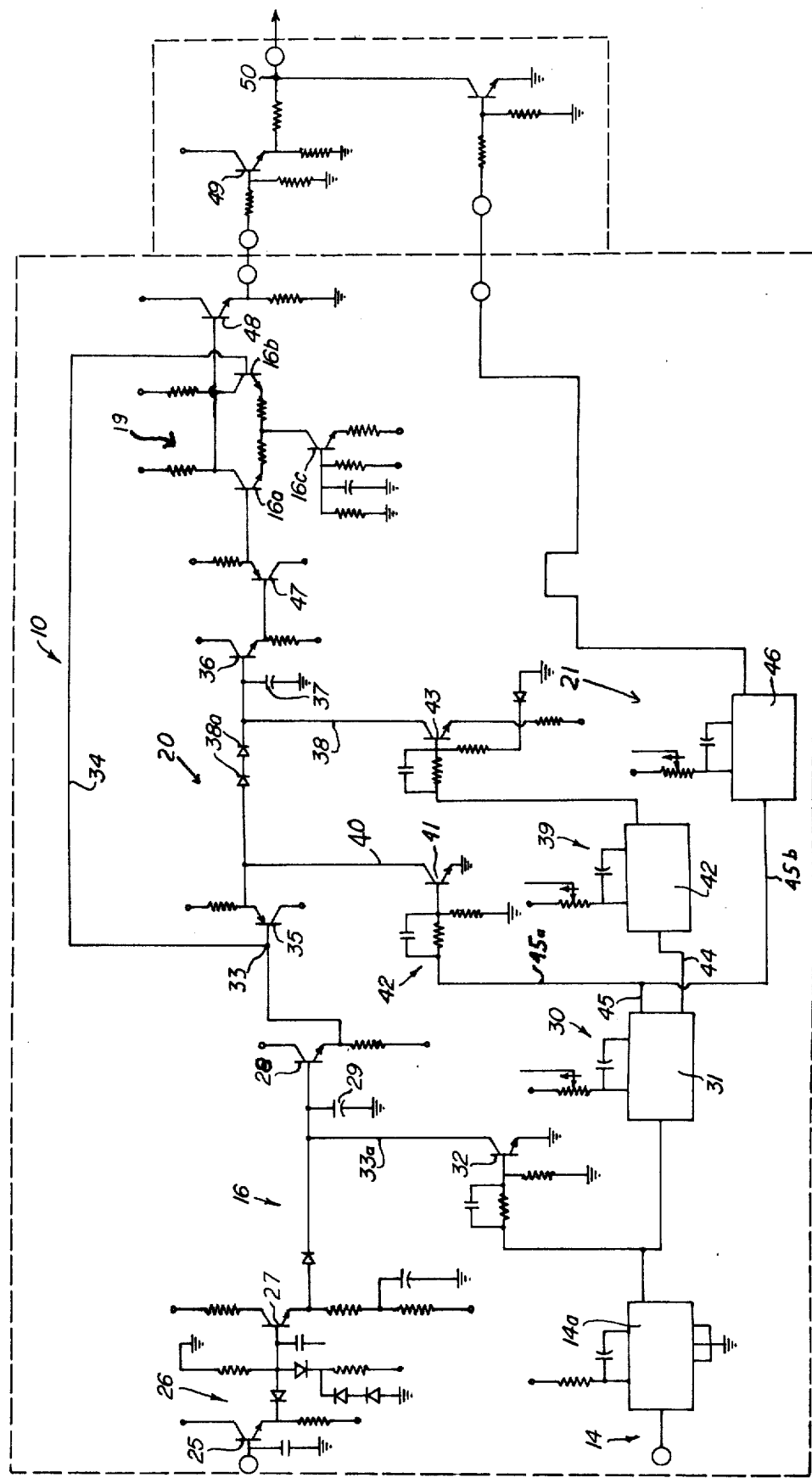

FIG. 1, is a block schematic view of two series connected filter-discriminator circuits of the present invention, the first such filter-discriminator circuit arranged to receive an input signal consisting of a train of pulses from a Perturbation Detector;

FIG. 2, a circuit diagram of the first filter-discriminator circuit of FIG. 1; and FIG. 3, a number of representations of signals identified as (A) through (E), each representing signal conditions measured at selected points in the block schematic view of FIG. 1. DETAILED DESCRIPTION Referring now to the drawings:

In FIG. 1 is shown a block schematic view of two filter-discriminator circuits 10 of the present invention serially connected to one another, the first filter-discriminator connected to receive an input train of pulses like those shown in (A) of FIG. 3, from a perturbation detector 11. The perturbation detector 11, shown herewith should be understood to be like that shown and described in my co-pending application for U.S. Patent application Ser. No. 381,549 that is filed simultaneously with the present application for U.S. Patent.

While, as shown herein, a preferred utilization of the filter-discriminator circuit of the present invention is for processing a train of signal pulses emanating from the perturbation detector, it should be readily apparent from the discussion to follow that the invention should not be limited to an application to any particular train of pulses generation means. Rather, the circuit of the present invention is uniquely suited for processing and discriminating signal pulses of unequal amplitude, amplitude modulated signals, off from a carrier. Conceivably, the circuit of the present invention could be used as a very sharp high pass filter capable of separating most amplitude modulated signals, or the like, off from a variety of carriers. Some such carriers that could be processed by the present invention could include radio frequencies and even laser beams.

Referring to FIG. 1, while two serially connected filter-discriminator circuits 10 are shown as a preferred arrangement of the present invention, providing in that hook up relatively large amplitude signal pulses per changes in amplitude of adjacent input signal pulses, it should be realized that a single filter-discriminator circuit 10 could provide a satisfactory signal output for many triggering functions. Therefore, the second filter-discriminator 10 is shown herein enclosed in a box formed of broken lines to indicate that it is an optional inclusion. Also, as the two filter-discriminator circuits are identical, the explanation of one should be taken as an explanation of the other also.

The perturbation detector 11 supplies a train of pulses as represented by (A) of FIG. 3. That train of pulses (A) is shown to contain pulses A' of like amplitude and one pulse A'' of lesser amplitude than its neighboring pulses, which train of pulses (A) is representative of a signal output from a scanning array 12 of the perturbation detector 11, FIG. 1. The single lesser amplitude pulse A'' in that train of pulses (A) represents a lesser amount of light striking a photo sensitive device in the scanning array 12 than the amount of light striking the other photo sensitive devices therein. A lens, FIG. 1, is arranged opposite to a face 12a of the scanning array, focusing light passing through the lens onto photo sensitive devices, not shown located on the scanning array face 12a. The passed light, prior to its entering the lens 13, is emitted from a light source, not shown, and travels through a transparent or translucent item under inspection, not shown. Should a crack, flaw, blemish, foreign object, or the like, be present in that item, then the light passing through such an obstruction would either be dissipated or gather light passed therethrough into that obstruction. The lens receiving light from that item, focuses that light onto the photo sensitive devices, one or more of the devices receiving that lesser or greater light from that portion of the item wherein the obstruction is present, producing when serially interrogated with the other photo sensitive devices, a signal or pulse output having an amplitude that is either greater or lesser in amplitude than adjacent pulses produced in the interrogation. As will be explained later herein, the circuitry of the present invention compares differences in signal pulse amplitude and therefore can sense either pulses of greater or lesser amplitude compared to adjacent pulses.

A clock is provided and connected through line 14a to the scanning array 12, passing signals thereto that serially interrogate the photo sensitive devices, not shown, producing the train of pulses (A) of FIG. 3. The train of pulses (A) then pass from the scanning device and are amplified by amplifier 15. Thereafter, the signal output passes into a first sample and hold circuit 16 of the first filter-discriminator circuit 10.

Within the first sample and hold circuit 16, as will be explained in detail later herein, the train of pulses (A) is processed, the output therefrom being a square wave signal (B), FIG. 3, wherein the uniform spike pulses A' of the train of pulses (A) are processed into uniform block waves B', and the lesser amplitude pulse A'' appears as the lesser amplitude block wave pulse B''.

The signal (B) output from the first sample and hold circuit 16 then passes to a junction 17, whereat the signal is passed through line 18 into one side of a difference amplifier 19, and into a second sample and hold circuit 20. The block wave signal is held for approximately the time interval between pulses, with the period of the block wave signal also being somewhat extended, and is thereafter passed to the opposite side of the difference amplifier 19, entering opposite to the signal input from the first sample and hold circuit 16. The output block wave signal from the second sample and hold circuit 20 is shown as (C) in FIG. 3.

The difference amplifier 19, shown as a triangular shaped block in FIG. 1, receives, at opposite points, the output signals of the first and second sample and hold circuits, comparing the signals against one another. The signal comparison produces an output signal containing signal spikes whose amplitudes equal the differences between the signal strength or amplitude of adjacent block wave signals passed from the first and second sample and hold circuits. This signal output is represented by (D) of FIG. 3. In (D) the straight line portion D' represents point of like amplitude in the compared signals and the spikes D'' are the resultants of comparisons of points of different amplitude in the compared signal, it being realized that such comparisons are actually between adjacent pulses in the original train of pulses input (A). Shown in FIG. 3, broken lines F and G are drawn between the block wave signals (B) through (E) to indicate time increments whereat comparisons of points of equal amplitude on the two signals are made, and broken lines H and I represent time increments whereat comparisons of points of unlike amplitude are made.

It should be noted that, in actual practice, perfect signal filtering in the difference amplifier 19 is impossible with a number of undesirable transient signals emerging along with the desired pulses D''. The straight line portion D' of signal (D) would therefore, in actuality, contain a number of low amplitude pulses, which pulses are due to imperfect filtering and to the fact that different portions of the item under inspection may pass light differently. To eliminate such low amplitude transients, the circuit provides a blanker signal from a blanker 21, shown as a block, that receives timing signals from the clock 14 and imposes its output onto the output from the difference amplifier to eliminate transients therein.

The product of the first filter-discriminator circuit 10 signal (D), of course, contains individual pulses D'' as the product of signal comparison, which pulses can be used to perform switching or trigger function, for operating related equipment, as for example, devices for removing the item sensed as having an imperfection from a moving line of such items. Pulses D'' may however, not be sufficiently refined to assure that they will have sufficient signal strength to perform such functions. This deficiency can be corrected by serially adding a second filter-discriminator circuit 10 to the first, which addition is shown in FIG. 1 and is surrounded by a box formed of a broken line to indicate that it is an optional inclusion.

With the second filter-discriminator circuit 10 installed to the first, as shown in FIG. 1, the product of the signal (D) passage therethrough will be like the signal (E) of FIG. 3. In such passage the signal pulses D'' are converted into signal pulses E'' shown to extend well above and below the signal axis E', which signal pulses E'' represent double derivatives of the comparison of the lesser amplitude pulse A'' with the pulses A' on either side thereof in the train of pulses (A).

FIG. 2 shows a schematic diagram of the filter-discriminator circuit 10. For purposes of this discussion we will assume that this circuit represents the first filter-discriminator circuit 10, that receives the train of pulses (A), FIG. 3, as an input onto the base of an emitter follower device 25 thereof. The emitter follower device 25, and the resistor and diode components shown associated therewith make up a direct current level shifter 26, wherein the input signal is shifted. From the direct current level shifter 26, the train of pulses (A) pass into an amplifier 27, having a near unity gain. Continuing through the circuit, between the amplifier 27 and a solid state device 28, is arranged a capacitor 29, which capacitor, along with the amplifier 27 and solid state device 28 make up the first sample and hold circuit 16. In the first sample and hold circuit 16, as shown in the signal representation (B) of FIG. 3, the pulses A' and A'' of the train (A) are stretched horizontally into B' and B'' respectively. This is accomplished by the capacitor 29 holding each incoming pulse A' and A'' until a dumping signal is received whereat the charge on the capacitor is dumped, generating the block wave signal (B). The dumping signal is provided by a dumping circuit 30 connected thereto that consists of a mono-stable multi-vibrator integrated circuit device 31, solid state device 32, and associated components connected together and receiving signals from the clock 14 to synchronize dumping signal outputs with the input train of pulses (A). The clock 14 is shown herein as a circle connected to another mono-stable multi-vibrator integrated circuit 14b, and associated components, each clock pulse produced therein triggering a time of desired output pulse from the integrated circuit 14b. Signals generated in the dumper circuit 30 flow therefrom through line 33a, intersecting the signal path of the train of pulses (A) and causing the signal stored in the capacitor 29 to be dumped.

The dumper circuit 30 provides the impetus for rapidly discharging the capacitor 29 back to its starting potential, which discharge produces block wave signal (B) that passes from the solid state device 28, shown herein as an NPN device, into a junction 33. At the junction 33, the signal enters a line 34 that connects at its opposite end to one side of the difference amplifier 19. The difference amplifier 19, shown here, consists of two NPN solid state devices 16a and 16b, whose emitters are each connected in series to an NPN solid state device 16c and related components.

The block wave signal (B) in addition to traveling directly to the difference amplifier travels also from the junction 33 into another solid state device 35 that is shown herein as a PNP device. Different types of junction devices, i.e. NPN and PNP devices are used as solid state devices 28 and 35 to avoid a D.C. signal drop when passing the signal (B) therethrough.

The solid state device 35, in turn, connects to the base of an NPN solid state device 36 and in series with a capacitor 37 that, like the capacitor 29, has its opposite side at ground potential. The solid state devices 35 and 36 and capacitor 37 make up the second sample and hold circuit 20, which circuit receives dumping pulses through a line 38 from a dumper circuit 39, blocker pulses through a line 40 from a solid state device 41, and connects to filter circuit 42.

The dumper circuit 39, like the already described dumper circuit 30, consists of a mono-stable multi-vibrator integrated circuit device 42, solid state device 43, and associated components. Clock pulses are passed from the clock 14, through the mono-stable multi-vibrator device 31 and through a line 44 and into the mono-stable multi-vibrator device 42 of the dumper circuit. Simultaneously, clock pulses are also supplied to the blocker pulse generating solid state device through line 45 and branch 45a, which line 45 supplies also a branch 45b that connects to another integrated circuit 46 that supplies blanker pulses, as will be explained in detail later herein, to the output of the difference amplifier 19.

The signal (B) passing from the solid state device 35 has blocker signal pulses imposed thereon that are timed so as to oppose a voltage buildup across the capacitor 37. The blocker signals hold the collector emitter of the device 35 at ground potential except during periods in which it is desirable that the capacitor 37 take a charge. At such times, assuming a potential difference exists between the device 35 and capacitor 37, a flow therebetween will occur. That flow, passing through diode gates 38A will charge the capacitor 37 to its peak value. At that peak value, even should the potential on device 35 decrease, a reverse flow is blocked by diodes 38a. The capacitor 37 will thereby hold its charge until the dumped circuit 39 generates a signal that is passed to the capacitor 37 to cause it to immediately discharge, which discharge is like the discharge from the first sample and hold circuit 16, appearing like the block wave signal (C) of FIG. 3.

The block wave signal (C) thereafter passes to another solid state device 47, effecting signal transfer therebetween without any direct current signal drop because the solid state devices 36 and 47 are different types of junction devices, i.e. device 36 is an NPN device and device 47 is a PNP device. The signal from the second sample and hold circuit 20, that has passed through the solid state device 47, is then imposed on the base of one of the solid state devices of the difference amplifier, opposite to the wave form signal received directly from the first sample and hold circuit 16. Shown in FIG. 2, the signal from the first sample and hold circuit 16 enters the base of the solid state device 16b and the signal from the second sample and hold circuit 20 flows into the base of the solid state device 16a.

Within the difference amplifier 19, the signal inputs to the solid state devices are compared, the output therefrom reflecting differences sensed in the comparison of signal amplitudes. Should no differences exist, then the output would be a straight horizontal line D'. The signal either a straight line D' or a signal containing pulses D'', (D) shown in FIG. 3, passes from the difference amplifier 20 and onto the base of an emitter follower 48 and thence to the base of a second emitter follower 49. The emitter follower devices 48 and 49 make up a level shifting circuit wherein the signal is attenuated.

The signal passed out from the emitter of the emitter follower 49 has a blanker signal imposed thereon at a junction 50. The blanker signal emanates, as has already been mentioned herein, from the integrated circuit 46, which, of course, has received timed pulses from the clock 14. The purpose of which blanker signal so generated is to blank out transcient signals that may be present in the output from the emitter follower 49. Specifically, although the difference amplifier is intended to eliminate all signals but those of different amplitude, in practice, the output therefrom will contain a number of low amplitude interference signals. These signals are undesirable as they could possibly interfer with later sensing of the pulses representative of differences in input pulse amplitudes. Therefore, it is desirable to provide a blanker signal that is timed to provide a sample gate through which the signal will pass at intervals when comparison is desired. Broken lines I, F, G, and H in FIG. 3 represent such sample intervals.

Should a second filter-discriminator circuit be serially coupled to the described first filter-discriminator, as is preferred, the output therefrom will be a double derivative of the input train of pulses (A). Such a signal output is shown at (D) in FIG. 3, pulses E'' having much greater signal amplitudes than do the pulse outputs D'' from the first filter-discriminator circuit, and therefore would be significantly more reliable for use in triggering apparatus. Such triggering apparatus could involve a timer or kicker arrangement, not shown, to eliminate the item having the imperfection therein, from the other items that are not so marred.

Thus far, the present invention in a filter-discriminator circuit has been described as being useful for detecting flaws, foreign objects, and the like in transparent or translucent items, implying bottles constructed of glass or even plastic. It should also be realized that the present invention, along with the perturbation detector of my co-pending application for U.S. patent could be useful in examining a moving film-type tape or the like. Such an inspection process could involve passing the tape in front of a light source, light passing therethrough and into the lens 13 of FIG. 1, producing a train of pulses like that already described for later processing.

It should also be understood that addition to flaw and foreign object detection in transparent and translucent bottles and film, the present invention could have a variety of signal discrimination applications. Conceivably, the present invention could be used to separate amplitude modulated signals off from a carrier signal. The present invention should therefore not be limited to any particular application or use.

Although a preferred embodiment of our invention has been herein described, it is to be understood that the present disclosure is made by way of example and that variations are possible, without departing from the scope of the hereinafter claimed subject matter, which subject matter we regard as our invention.

We claim:

1. A filter-discriminator circuit comprising:
    means for providing a train of pulses, the amplitude of each of which pulses is to be compared against adjacent pulses in the train;
    a first sample and hold circuit that receives the train of pulses and extends the period of the pulses in said train;
    a second sample and hold circuit adapted to receive the signal output from said first sample and hold circuit and having means for delaying the signal passage therethrough by approximately the period of one input pulse;
    a difference amplifier that receives the signal outputs from both the first and second sample and hold circuits comparing these signal outputs with one another producing, from that comparison, an output signal having pulses whose amplitudes equal the differences in amplitudes between compared pulses; and
    clock means connected to said means for providing a train of pulses and to the difference amplifier for synchronizing the signal outputs with the input train of pulses.

2. A filter-discriminator circuit as recited in claim 1, further including
    means for providing a signal for blanking out transient signals from the signal output of the difference amplifier.

3. A first filter-discriminator circuit as recited in claim 1, including
    a second filter-discriminator circuit connected in series with a said first filter-discriminator circuit, the signal output from said first filter-discriminator circuit being further compared within said second filter discriminator circuit, producing a signal output equal to the double derivative of the input train of pulses.

4. A filter-discriminator circuit as recited in claim 1, wherein
    the first and second sample and hold circuits each contain capacitors that are charged by each incoming pulse, which charge is held, and then dumped by the introduction of a dumping pulse; and
    means connected to the clock means and in series with each said capacitor for providing timed dumping pulses.

* * * * *